United States Patent [19]
Dysarz

[11] Patent Number: 5,997,507
[45] Date of Patent: Dec. 7, 1999

[54] BIASED SPRING HARD NEEDLE RETRACTABLE IV CATHETER

[76] Inventor: Edward D. Dysarz, 11423 Triola La., Houston, Tex. 77072

[21] Appl. No.: 09/130,969

[22] Filed: Aug. 7, 1998

[51] Int. Cl.$^6$ .................................................. A61M 5/178
[52] U.S. Cl. ........................ 604/161; 604/164; 604/168; 604/110
[58] Field of Search .................................. 604/110, 158, 604/164, 168, 171, 181, 187, 195, 263, 198, 161

[56] References Cited

U.S. PATENT DOCUMENTS

| | | |
|---|---|---|
| 3,008,570 | 11/1961 | Roehr et al. . |
| 3,107,785 | 10/1963 | Roehr . |
| 3,295,633 | 1/1967 | Bartner et al. . |
| 3,306,291 | 2/1967 | Burke . |
| 4,300,678 | 11/1981 | Gyvre et al. . |
| 4,356,822 | 11/1982 | Winstead Hall . |
| 4,425,120 | 1/1984 | Sampson . |
| 4,639,249 | 1/1987 | Larson . |
| 4,655,751 | 4/1987 | Harbaugh . |
| 4,664,654 | 5/1987 | Strauss . |
| 4,702,738 | 10/1987 | Spencer . |

Primary Examiner—Wynn Wood Cuggins
Assistant Examiner—Deborah Blyveis

[57] ABSTRACT

A intravenous catheter device having a biased spring hard needle, disposed in a soft catheter. The biased spring hard needle is held within an elongated hollow barrel wherein the biased spring hard needle is extended past the first end of the soft catheter, and is further disposed in the inside of the soft catheter and further extends past the first end of the elongated hollow barrel wherein the biased spring hard needle is pulled into an almost straight line wherein the second end of the biased spring hard needle is fixed to an end cap at the second end of the elongated hollow barrel. The biased spring hard needle is held within the soft catheter and the elongated hollow barrel by a latch means. When the latch means is disengaged with the biased spring hard needle, the spring section of the biased spring hard needle that is near the second end of the biased spring hard needle instantly withdraws the first end of the biased spring hard needle out of the soft catheter and further withdraws the first end of the biased spring hard needle out of the first end of the elongated hollow barrel wherein the first end of the biased spring hard needle cannot accidentally prick or injury a person thereby preventing an accidental injection of bacteria, virus or other undesirable material into a person.

10 Claims, 4 Drawing Sheets

BIASED SPRING HARD NEEDLE RETRACTABLE IV CATHETER

BACKGROUND OF THE INVENTION

There are several types of safety intravenous catheter designs. Most of the designs are similar to syringes or blood sampling devices that are available today. One such design is shown in a patent issued to JAGGER et al on Jun. 3, 1986 U.S. Pat. No. 4,592,744. This is a safety blood sampling device however it requires two (2) hands to operate or to cover the needle cannula.

Blood samples are also taken with syringes and there are also many safety syringes available. Some of these designs have a sleeve or sheath that will cover the needle after it has been used. Some typical designs with sleeves or sheaths are Z.M. ROEHR et all U.S. Pat. No. 3,008,570, Z.M. ROEHR U.S. Pat. No. 3,107,785, BARTNER, et al U.S. Pat. No. 3,895,633, G.K. BURKE U.S. Pat. No. 3,306,291, GYURE et al U.S. Pat. No. 4,300,678, WINSTEAD HALL U.S. Pat. No. 4,356,822, SAMPSON U.S. Pat. No. 4,425,120, LARSON U.S. Pat. No. 4,639,249, HARBAUGH U.S. Pat. No. 4,655,751, STRAUSS U.S. Pat. No. 4,664,654, BRAGINETZ U.S. Pat. No. 466,435, SPENCER U.S. Pat. No. 4,702,738, MILORAD U.S. Pat. No. 4,702,739, SPENCER U.S. Pat. No. 4,801,295, PONCY U.S. Pat. No. 4,816,022, and HUGHES U.S. Pat. No. 4,840,619.

Other designs have a retractable needle such as WELTMAN U.S. Pat. No. 3,306,290, and DENT U.S. Pat. No. 4,392,859. These designs do not have a means whereby the needle is extended from the syringe and held in place in a positive and rigid position in order to first inject the needle prior to injecting the medication. Still other designs have methods of bending to render the needle harmless after the medication has been injected. Most of these designs have one major purpose and that is to prevent the spread of infectious diseases such as aids, hepatitis, or other diseases from an accidental injection with a contaminated needle into others after the needle of the syringe was inserted into a patient with the above mentioned disease. These various designs all work well to a degree, but they all fall short of there intended purpose during the act of covering the needle, or removing the needle, which requires two hands.

All of these designs require at least two hands to operate. The use of two hands to cover the contaminated needle is most unsatisfactory in that during the act of placing a second hand on the intervenes catheter device or syringe, the person holding the intravenous catheter device or syringe in one hand may be bumped and accidentally inject the needle into there other hand before it can grasp the syringe. Other accidental jabbing or injections can happen in an ambulance where just as a person tries to grasp the contaminated intravenous catheter device or syringe, the ambulance can hit a bump in the road causing the person holding the intravenous catheter device or syringe to accidentally stick another person or themselves with the contaminated needle. The need has developed for an intravenous catheter device or syringe that will cover the contaminated needle with the use of only one hand.

SUMMARY

It is the object of this invention to provide an intravenous catheter device wherein the needle of the intravenous catheter device is retracted into the barrel of the intravenous catheter device and protects others from an accidental pricking after it has been used; the needle can be retracted into the barrel with the use of only one hand and that one hand being the hand that was used to inject the needle cannula into a patient.

Another object of the present invention is to render the needle cannula of the intravenous catheter device useless after the needle is retracted into the barrel of the intravenous catheter device to prevent the accidental reuse of the contaminated needle or to further prevent the reuse and abuse by users of illicit drugs.

It is still another object of the present invention to further prevent the accidental release of the needle cannula after the needle cannula is in the barrel of the intravenous catheter device.

The foregoing and other objects and advantages are attained by a device, an elongated hollow barrel, a spring needle cannula, hub post and an end cap in combination with a latching means wherein when said intravenous catheter is used to inject a needle cannula into a vein in the body or part of the body in order to inject medication or other fluid at a consistent rate into the body, the latch means is released and the biased spring needle cannula further pulls the spring needle cannula into the elongated hollow barrel of the intravenous catheter device rendering the contaminated spring needle cannula harmless to prevent the accidental pricking of others and to prevent a contaminated spring needle cannula from being released from the barrel of the intravenous catheter device.

The features of the present invention can be best understood together with further objects and advantages by reference to the following descriptions taken in connection with accompanying drawing, wherein like numerals indicate like parts.

BRIEF DESCRIPTION OF THE DRAWINGS

FIG. 5 is a section elevation view of the device showing the needle release button being pressed in.

DETAILED DESCRIPTION OF THE PREFERRED EMBODIMENT

Figure 1:
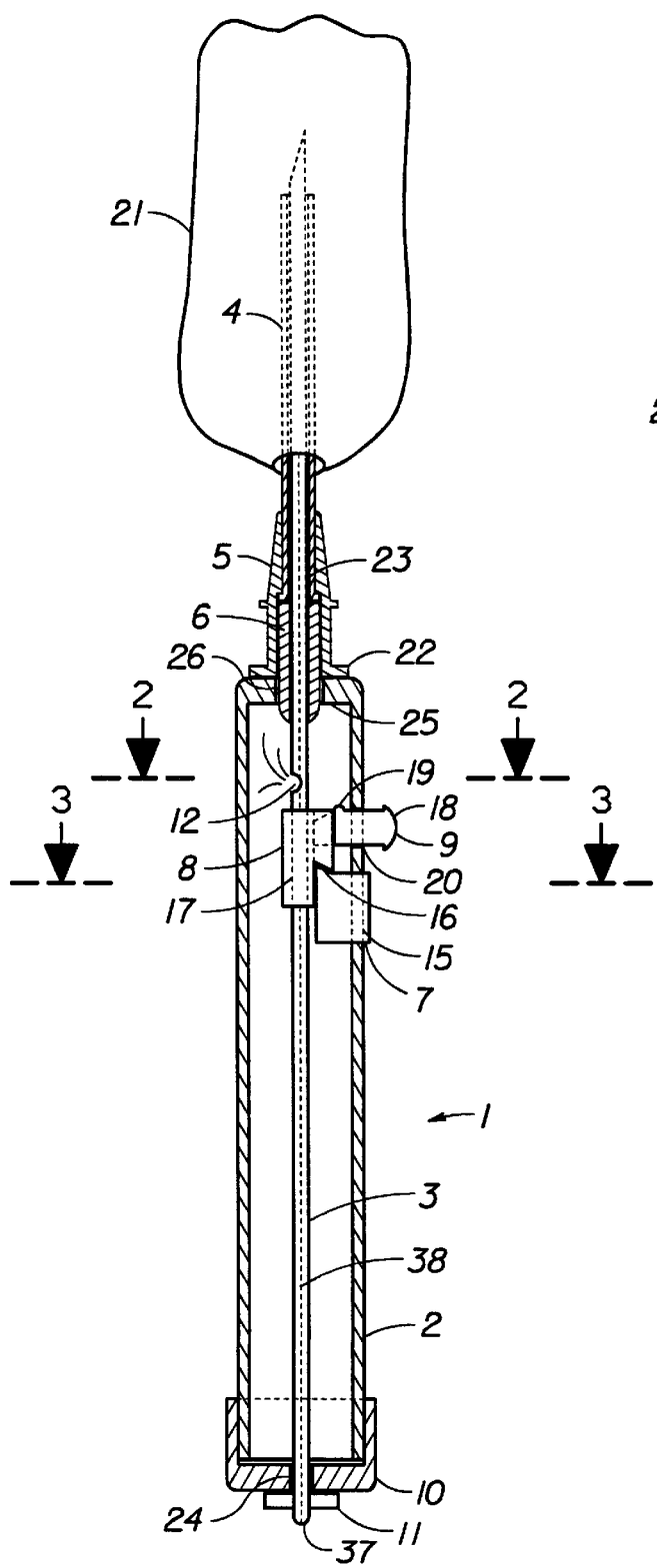
FIG. 1 is a section elevation view of the device of the preferred embodiment of the present invention.

Referring to FIG. 1 there is shown a section elevation view of the device 1 of the preferred embodiment.

The intravenous catheter device 1 is comprised of an elongated hollow barrel 2 that has a first end, a second end and is circumferential in section with an inside surface and an outside surface. A latch foundation 7 is shown suitably fixed to the elongated hollow barrel 2 wherein the latch foundation 7 is inserted into the first hole 15 formed in the elongated hollow barrel 2 near the first end of the elongated hollow barrel 2. The first hole 15 extends from the outside surface to the inside surface of the elongated hollow barrel 2. The latch foundation 7 is inserted into the first hole 15 wherein the latch foundation 7 is suitably fixed to the first hole 15 by adhesive welding or other suitable means. The latch foundation will be described in greater detail in FIG. 3 and FIG. 4.

The inclined plane latch 8 is shown with a first end, a second end, a third end, a fourth end and an inclined plane 16. A needle hole 17 is formed in the inclined plane latch 8 wherein the needle hole extend from the first end to the second end of the inclined plane latch 8. The biased spring hard needle 3 is suitably disposed in the needle hole 17 wherein the biased spring hard needle 3 is suitably fixed to the inclined plane latch 8 by adhesive, welding or some other suitable means. The inclined plane latch 8 is shown suitably attached to the latch foundation 7.

The needle release button 9 is shown with a first end and a second end. A depressor knob 18 is shown at the first end wherein a finger of thumb will most likely press the depressor knob 18 to disengage the inclined plane latch 8 from the latch foundation 7. The stop knob 19 is shown at the second end of the needle release button 9. The stop knob 19 prevents the needle release button 9 from falling out of the needle release hole 20. The needle release hole 20 is shown near the first end of the elongated hollow barrel 2 and extends from the inside surface to the outside surface of the elongated hollow barrel 2.

The soft catheter 4 is shown with a first end and a second end. The first end of the soft catheter 4 is shown inserted into a body 21 and the second end of the soft catheter 4 is shown suitably fixed to the first end of the first hub 5. The second end of the first hub 5 is a hollow tube and is disposed about the first end of the hub post 6. The first hub 5 is held in place and is supported on the hub post 6 by friction which will allow the hub post 6 to pull out of the first hub 5 with little force. The first hub 5 has a hub flange 22 at the second end of the first hub 5 to allow the first hub 5 to be fastened to an intravenous tube that is not the subject of this invention. As stated, the first end of the hub post 6 disposed in the inside surface of the second end of the first hub 5 and held in place by friction or some other suitable means. A hub post hole 23 is formed in the hub post 6 wherein the hub post hole 23 extends from the first end of the hub post 6 to the second end of the hub post 6. The biased spring hard needle 3 is disposed in the hub post hole 23 and suitably fixed to the hub post hole 23 by adhesive, welding or friction or some other suitable means by design choice.

A elongated hollow barrel flange 25 is shown at the first end of the elongated hollow barrel 2 and a flange hole 26 is shown formed on the elongated hollow barrel flange 25 that extends from the first side to the second side of the elongated hollow barrel flange 25.

The biased spring hard needle 3 is essentially comprised of a first section from the point 35 at the first end, to the second end of the inclined plane latch 8. The second section of the biased spring hard needle essentially extends from the second end of the inclined plane latch 8 to the loop 37. The second section of the biased spring hard needle is mostly comprised of the biased spring. The first section has a first end and a second end and the second section has a first end and a second end.

The first section of the biased spring hard needle 3 is shown extending past the first end of the soft catheter 4 wherein the first section of the biased spring hard needle 3 is loosely disposed in the soft catheter 4. The second end of the first section of the biased spring hard needle 3 is further disposed in and suitably fixed to the hub post 6 and the inclined plane latch 8 at the second end of the first section wherein the second section of the biased spring hard needle 3 extends to the second end of the elongated hollow barrel 2 and is shown extending through a cap hole 24 formed in the end cap 10 wherein the second end of the second section of the biased spring hard needle 3 is hooked around an end bar 11. The second end of the second section of the biased spring hard needle 3 is hooked around the end bar 11 to allow a biase or tension to exist between the latch foundation 7 and the end bar 11. Although the end bar 11 is shown as a suitable means for holding the second end of the biased spring hard needle 3 other means such as adhesive, welding or other suitable means could be used to hold the second end of the biased spring hard needle 3 to the end cap 10 or the second end of the elongated hollow barrel 2.

A fluid release hole 12 is shown formed in the side of the biased spring hard needle 3 to allow blood or other fluid to flow out of the cannula 38 formed on the inside of the biased spring hard needle 3. If the biased spring hard needle 3 is required to be hollow the blood flow out of the fluid release hole 12 will inform a person inserting the biased spring hard needle 3 into a body if the biased spring hard needle 3 is in a vein, artery or whatever it may be inserted into. The fluid release hole 12 may or may not be necessary to the operation of the device.

The biased spring hard needle 3 acts as a transverse spring and maintains preassure on the needle release button 9 through the included plane latch 8 to keep the needle release button 9 projecting out of the elongated hollow barrel 2.

Figure 2:
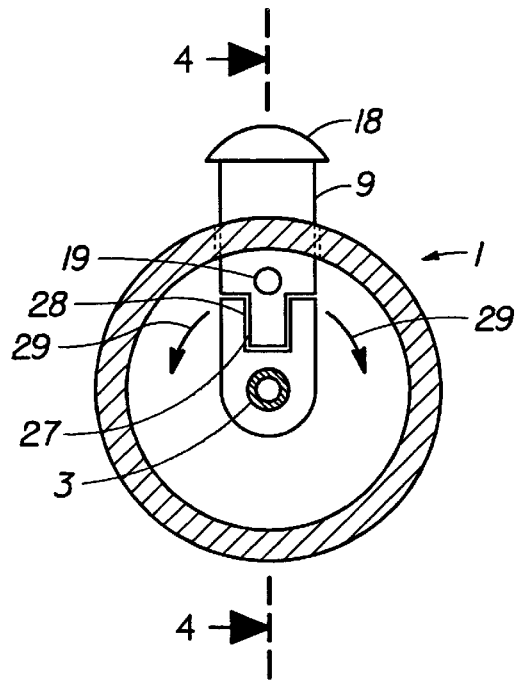
FIG. 2 is a section elevation view of the device as taken through FIG. 1.

Referring to FIG. 2 there is shown a section elevation of device 1 as taken through FIG. 1.

The elongate hollow barrel 2 is shown as being circumferential in configuration, however it could be square, rectangular or any other configuration by design choice.

The needle release button 9 is shown with a first end and a second end. The depressor knob 18 is shown on the first end and the stop knob 19 is shown near the second end. An anti rotation guide 27 is shown at the second end of the needle release button 9. The anti rotation guide 27 is shown disposed in the anti rotation slot 28 formed in the inclined plane latch 8. The biased spring hard needle 3 with a cannula is shown suitably fixed to the inclined plane latch 8. The anti rotation guide 27 that is suitably disposed in the anti rotation slot 28 will prevent the inclined plane latch 8 from rotating 29 during use.

Figure 3:
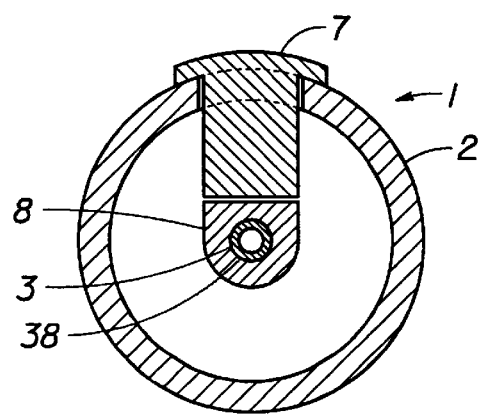
FIG. 3 is a section elevation view of the device as taken through FIG. 1.

Referring to FIG. 3 there is shown a section elevation of the device 1 as taken through FIG. 1.

The elongated hollow barrel 2 is shown supporting the latch foundation 7. The biased spring hard needle 3 with a cannula 38 is shown fixed to the inclined plane latch 8.

Figure 4:
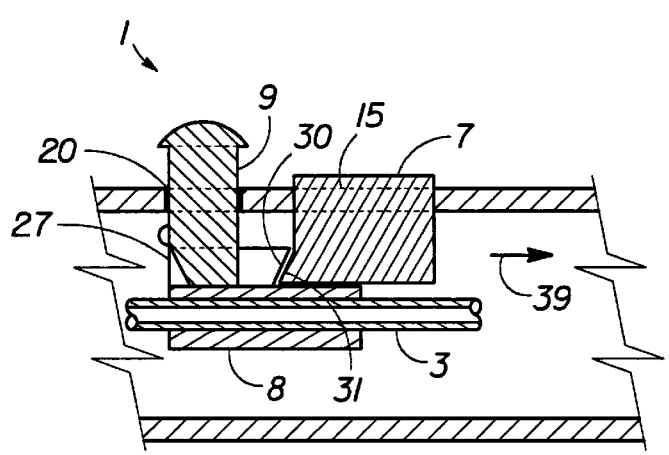
FIG. 4 is a section elevation view of the device as taken through FIG. 2.

Referring to FIG. 4 there is shown a section elevation of the device 1 as taken through FIG. 2.

The needle release button 9 is shown disposed in the needle release hole 20. The latch foundation 7 is shown fixed to the elongated hollow barrel 2 at the first hole 15. The anti rotation guide 27 is shown suitably disposed in the anti rotation slot 18 formed in the needle release button 9. The biased spring hard needle 3 is shown suitably fixed to the inclined plane latch 8.

The latch inclined plane 30 is shown pressed against and hooked to the foundation inclined plane 31. The biased spring hard needle 3 is pulling the inclined plane latch 8 and the latch incline plane 30 hard against the foundation inclined plane 31 of the latch foundation 7 thereby preventing the inclined plane latch 8 and the first end of the biased spring hard needle 3 from moving in a retract direction 39. Only the second end of the biased spring hard needle 3 is biased into a spring; the first end of the biased spring hard needle is a straight hard needle.

Figure 5:
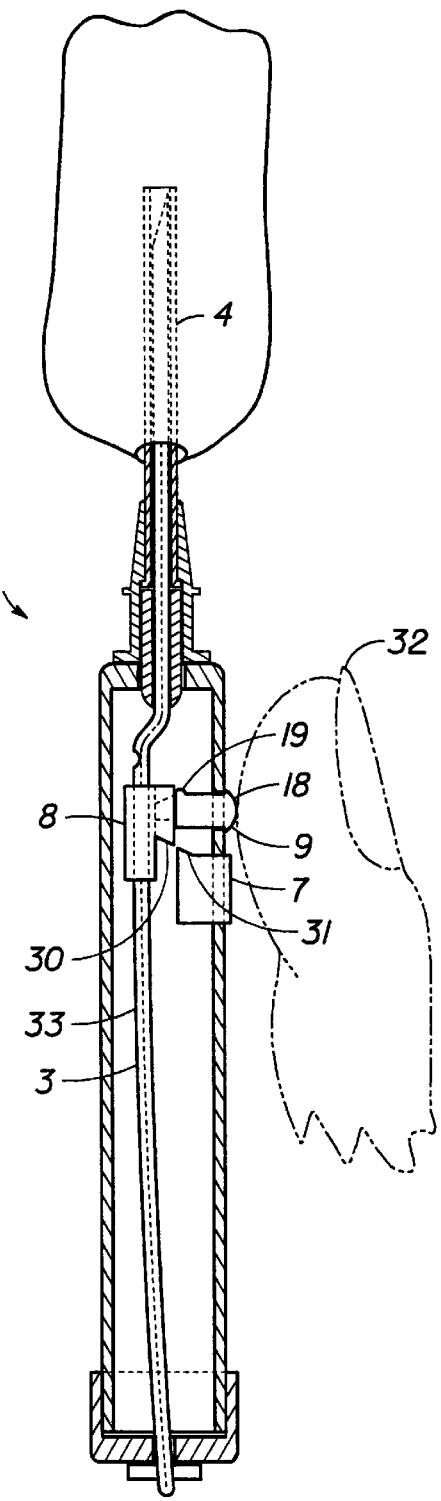

Referring to FIG. 5 there is shown a section elevation of the device 1 as it is about to be retracted.

A finger 32 or thumb is shown depressing the needle release button 9 therein thrusting the inclined plane latch 8 away from the latch foundation 7 and disengaging the latch incline plane 30 from the foundation incline plane 31. The biased spring hard needle 3 acts as a transverse spring and therefore resists the thrust from the finger 32 and the needle release button 9, however, the biased spring hard needle 3 deflects 33 some or bends some thereby releasing the hook like grasp that the latch inclined plane 30 had on the foundation inclined plane 31. The position shown in FIG. 5 should last only a brief moment as the biased second end of the biased spring hard needle 3 pulls the first end out of the soft catheter 4.

Figure 6:
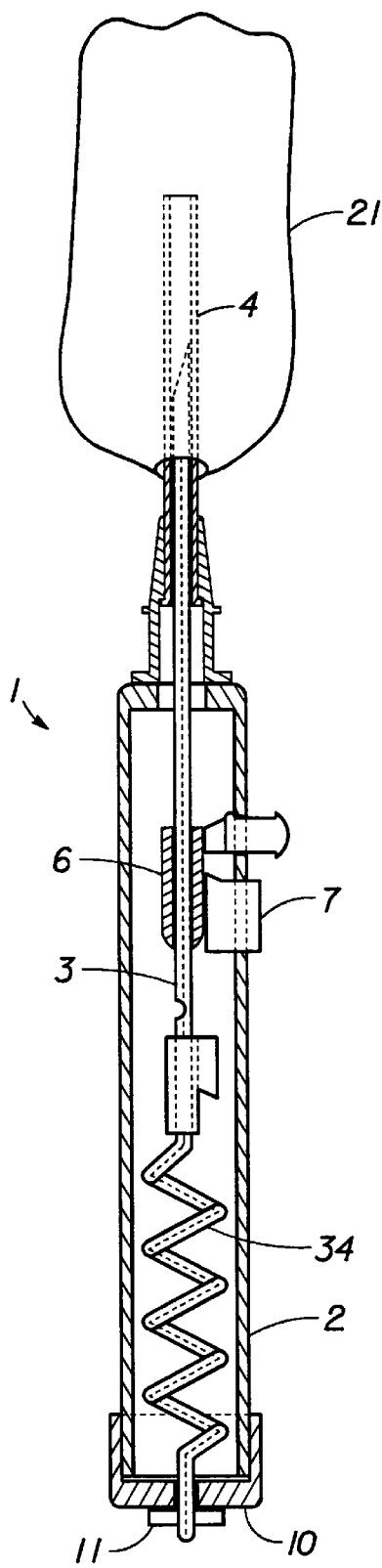
FIG. 6 is a section elevation view of the device showing the device being disabled.

Referring to FIG. 6 there is shown a continuation of the retraction of the biased spring hard needle 3 of the device 1.

The second end of the biased spring hard needle 3 is forming into a coil 34. The first end of the biased spring hard needle 3 is being withdrawn from the soft catheter 4 leaving the soft catheter 4 in the body 21. The second end of the hub post 6 is shown as tapered to prevent it from catching a corner of the latch foundation 7. Only the second end of the biased spring hard needle 3 is fixed to the second end of the elongated hollow barrel 2 by way of the end cap 10 and end bar 11.

Figure 7:
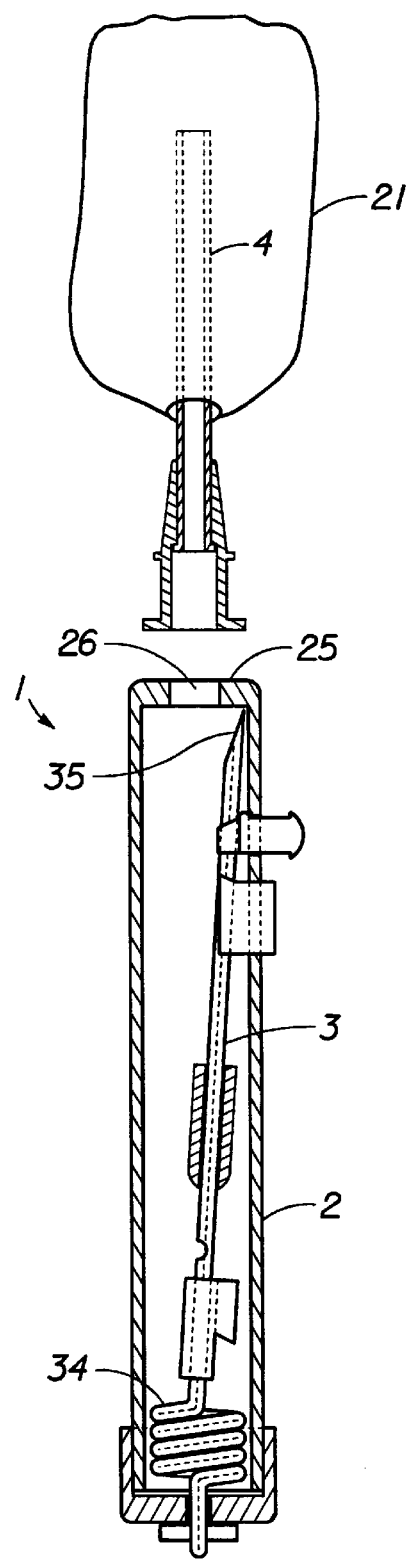
FIG. 7 is a section elevation view of the device disabled.

Referring to FIG. 7 there is shown a section elevation of the device 1 with the biased spring hard needle 3 retracted.

The biased spring hard needle 3 is no longer biased; the second end has formed into a coil 34 and is permanently pulling or holding the first end of the biased spring hard needle 3 inside of the elongated hollow barrel 2. The coil 34 is also causing the biased spring hard needle 3 to rest at an angle within the elongated hollow barrel 2 thereby preventing the point 35 at the first end of the biased spring hard needle 3 from re-entering the flange hole 26 formed in the elongated hollow barrel flange 25.

The soft catheter 4 is shown left in the body 21 where it will be suitably attached or fixed to other devices.

Figure 8:
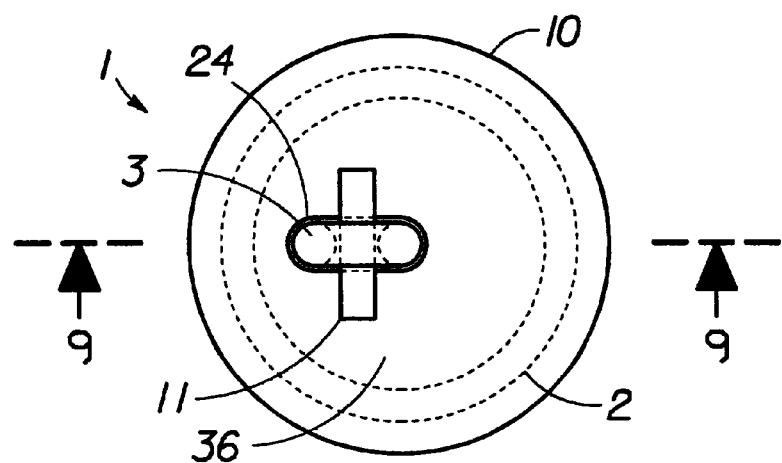
FIG. 8 is an end view of the end cap.

Referring to FIG. 8 there is shown a view of the end cap 10 of the device 1.

The cap hole 24 is formed at the second end of the end cap 10 and extends from the first side to the second side of the end cap cover 3. The second end of the biased spring hard needle 3 is formed into a loop or hook and extends through the end cap cover 36 wherein an end bar 11 is inserted into the loop or hook to capture and hold the biased spring hard needle 2. The end bar 11 is suitably fixed to the end cap cover 36 by adhesive, welding, rivets or other suitable means by design choice.

Figure 9:
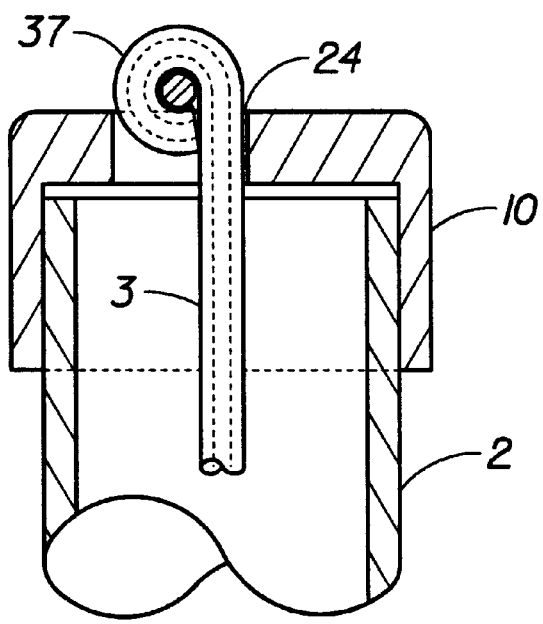
FIG. 9 is a section view as taken through FIG. 8.

Referring to FIG. 9 there is shown a section elevation of the end cap 10 as taken through FIG. 8.

The second end of the biased spring hard needle 3 is formed into a loop 37 wherein the entire loop 37 is disposed or could be disposed in the cap hole 24. The end cap 10 is suitably fixed to the second end of the elongated hollow barrel 2 by adhesive threads, rivets, or welding or other suitable means by design choice.

Although the system described in detail supra has been found to be most satisfactory and prefered, many variations are possible. For example the second end of the soft catheter may be provided with valves to suitably stop the flow of blood while other devices are being attached or removed from the soft catheter, or the latch means could be placed in another location.

Although the invention has been described with reference to the preferred embodiment, it will be understood by those skilled in the art, that additions, modifications, substitutions, deletions and other changes not specifically described, may be made in the embodiment herein, it should be understood that the details herein are to be interpreted as illustrative and are not in a limiting sense.

What is claimed as invention is:

1. An intravenous catheter device for inserting a hard needle and a soft catheter into a body and withdrawing said hard needle from said body and safely covering said hard needle for further disposal comprised;

an elongated hollow barrel with a first end a second end an inside surface and an outside surface, a latch foundation hole formed near the first end of said elongated hollow barrel wherein said latch foundation hole extends from said inside surface to said outside surface of said elongated hollow barrel and wherein a needle release hole is formed near said first hole wherein said needle release hole extends from said inside surface to said outside surface of said elongated hollow barrel;

an elongated hollow barrel flange formed on said first end of said elongated hollow barrel wherein said elongated hollow barrel flange has a first side and a second side and a flange hole is formed in said elongated hollow flange wherein said flange hole extends from said first side to said second side of said elongated hollow barrel flange;

an end cap wherein said end cap has a first end and a second end and wherein said second end has an end cap a cover with a first side and a second side and wherein a cap hole is formed in said end cap cover and wherein said cap hole extends from said first side to said second side of said end cap cover;

a needle release button with a first end and a second end wherein said needle release button has a depressor knob on said first end and said needle release button has stop knob near said second end and said needle release button is disposed in said needle release hole formed in said elongated hollow barrel;

a latch foundation with a first end a second end, third end a fourth end and a foundation incline plane near said first end of said latch foundation wherein said latch foundation is disposed in and fixed to said latch foundation hole formed in said elongated hollow barrel;

an inclined plane latch with a first end, a second end, a third end, and a fourth end and wherein a latch inclined plane is formed on said third end between said first end and said second end of said inclined plane latch and wherein a needle hole is formed in said inclined plane latch that extends from said first end to said second end of said inclined plane latch;

a hub post with a first end and a second end and wherein a hub hole is formed in said hub post and said hub hole extends from the first end of said hub post to said second end of said hub post and wherein said hub post is disposed in said flange hole formed in said elongated hollow barrel flange;

a soft catheter with a first end and a second end wherein said first end of said soft catheter is inserted into said body;

a first hub with a first end and a second end wherein said first end of said first hub is fixed to said second end of said soft catheter and wherein said first hub is hollow with an inside surface and an outside surface and wherein said second end of said inside of said first hub is disposed about said first end of said hub post;

a biased spring hard needle with a first section and a second section wherein said first section of said biased spring hard needle has a first end and a second end and wherein said second section of said biased spring hard needle has a first end and a second end and wherein a biased spring is formed on said second section of said biased spring hard needle and said first section of said biased spring hard needle is disposed in said soft catheter and said second end of said first section of said biased spring hard needle is further disposed in said hub hole formed in said hub post and wherein said biased spring hard needle is fixed to said hub post, and wherein said second end of said first section of said biased spring hard needle is disposed in said needle hole famed in said inclined plane latch and said biased spring hard needle is fixed to said inclined plane latch and wherein said second section of said biased spring hard needle is formed into a biased spring and said biased spring is pulled until said second section of said biased spring hard needle is essentially formed into an almost straight line and said second section of said biased spring hard needle is pulled into a biased spring and wherein said second end of said second section is fixed to said end cap and wherein said end cap is fixed to said second end of said elongated hollow barrel and wherein said latch inclined plane formed on said inclined plane latch that is fixed to said biased spring hard needle is slideably fixed and hooked to said latch inclined plane formed on said latch foundation thereby preventing said second section of said biased spring hard needle from recoiling into said second end of said elongated hollow barrel and wherein when said needle release button is depressed, said needle release button further thrusts against said inclined plane latch thereby causing said latch incline plane to slide off of said foundation inclined plane formed on said latch foundation thereby releasing said biased spring hard needle further allowing said biased spring formed on said second section of said biased spring hard needle to recoil or reform into a coil thereby withdrawing said first section of said biased spring hard needle from said soft catheter and further withdrawing said point formed on said first end of said first section of said biased spring hard needle wherein said point is withdrawn into said first end of said elongated hollow barrel past said second side of said elongated hollow barrel flange thus enclosing said biased spring hard needle within said elongated hollow barrel and said elongated hollow barrel flange.

2. The intrvenous catheter device of claim 1 wherein a fluid release hole is formed in said biased spring hard needle to allow blood or other fluid to be released from the cannula formed in said biased spring hard needle.

3. The intravenous catheter device of claim 1 wherein when said biased spring hard needle is withdrawn into said elongated hollow barrel, said soft catheter remains in said body.

4. The intravenous catheter device of claim 1 wherein said biased spring hard needle acts as a transverse spring and thereby prevents said needle release button from releasing said inclined plane latch until said needle release button is depressed.

5. The intravenous catheter device of claim 1 wherein an anti rotation guide is formed at the second end of said needle release button and wherein an anti rotation slot is formed in the fourth end of said latch foundation and wherein said anti rotation guide is disposed in said anti rotation slot thereby preventing said biased spring hard needle from rotating.

6. The intravenous catheter device of claim 1 wherein said second end of said hub post is tapered wherein said hub post will not catch on said latch foundation as said hub post is being withdrawn into said elongated hollow barrel.

7. The intravenous catheter device of claim 1 wherein said first hub is fixed to said hub post by friction thereby allowing said hub post to be withdrawn from said second end of said first hub as said hub post fixed to said biased spring hard needle is withdrawn into said elongated hollow barrel.

8. The intravenous catheter device of claim 1 wherein said second end of said biased spring hard needle is formed into a loop and wherein said loop is pulled past said second side of said end cap cover and wherein an end bar is inserted into said loop and wherein said end bar prevents said second end of said biased spring hard needle to be withdrawn into said second end of said elongated hollow barrel.

9. The intravenous catheter device of claim 1 wherein said end bar is fixed to said end cap with adhesive.

10. The intravenous catheter device of claim 1 wherein said second section of said biased spring hard needle is formed into said coil thereby preventing said first end of said first section of said biased spring hard needle from being withdrawn past said elongated hollow barrel flange.

* * * * *